(12) United States Patent
von Bahr et al.

(10) Patent No.: US 7,846,739 B2
(45) Date of Patent: Dec. 7, 2010

(54) APPARATUS AND METHOD FOR DIAGNOSTIC GAS ANALYSIS

(75) Inventors: Pontus von Bahr, Enskede (SE); Tryggve Hemmingsson, Sollentuna (SE); Anders Jakobsson, Sundbyberg (SE); Fredric Gustafsson, Solna (SE)

(73) Assignee: Aerocrine AB, Solna (SE)

( * ) Notice: Subject to any disclaimer, the term of this patent is extended or adjusted under 35 U.S.C. 154(b) by 1188 days.

(21) Appl. No.: 10/664,225

(22) Filed: Sep. 16, 2003

(65) Prior Publication Data
US 2004/0082872 A1   Apr. 29, 2004

(30) Foreign Application Priority Data
Sep. 16, 2002 (SE) ................. 0202742-3
Oct. 2, 2002 (SE) ................. 0202906-4

(51) Int. Cl.
*G01N 1/22* (2006.01)
(52) U.S. Cl. ............... 436/116; 436/177; 422/83; 422/84; 422/93; 600/532
(58) Field of Classification Search ............... 436/116, 436/177; 422/83, 84, 93; 600/532
See application file for complete search history.

(56) References Cited

U.S. PATENT DOCUMENTS 3,925,183 A * 12/1975 Oswin et al. ............... 204/411
4,927,517 A    5/1990 Mizutani et al.
5,922,610 A    7/1999 Alving et al.
6,039,251 A *  3/2000 Holowko et al. ............. 235/380
6,468,222 B1 * 10/2002 Mault et al. ................. 600/531
7,045,359 B2 *  5/2006 Birks et al. ................. 436/118
7,192,782 B2 *  3/2007 Roller et al. ................ 436/116
2002/0077765 A1  6/2002 Mault

FOREIGN PATENT DOCUMENTS

| DE | 19951204 A1 | 5/2001 |
|---|---|---|
| EP | 0904729 A1 | 3/1999 |
| JP | H08-512405 A | 12/1996 |
| JP | H11-160311 A | 6/1999 |
| JP | 2001-513677 A | 9/2001 |
| WO | WO-95/02181 A1 | 1/1995 |
| WO | WO-98/37804 A1 | 9/1998 |
| WO | WO 01/26547 | 4/2001 |

* cited by examiner

*Primary Examiner*—Lyle A Alexander
(74) *Attorney, Agent, or Firm*—Morrison & Foerster LLP

(57) ABSTRACT

A handheld, small but accurate and reliable device for diagnostic NO measurements using a NO sensor, where the parameters governing the taking of the sample are different from the parameters optimal for the accuracy of said NO sensor I described. By temporarily storing a portion of the exhaled air, and feeding this to the sensor at a flow rate adapted to the NO sensor, the accuracy and sensitivity of a system/method involving NO sensors, in particular electrochemical NO sensors, can be increased. The method for diagnostic NO measurements comprises steps for controlling the inhalation of NO free air, as well as the exhalation, both by built-in means and by audible and/or visual feedback to the patient.

20 Claims, 1 Drawing Sheet

APPARATUS AND METHOD FOR DIAGNOSTIC GAS ANALYSIS

Figure 1:
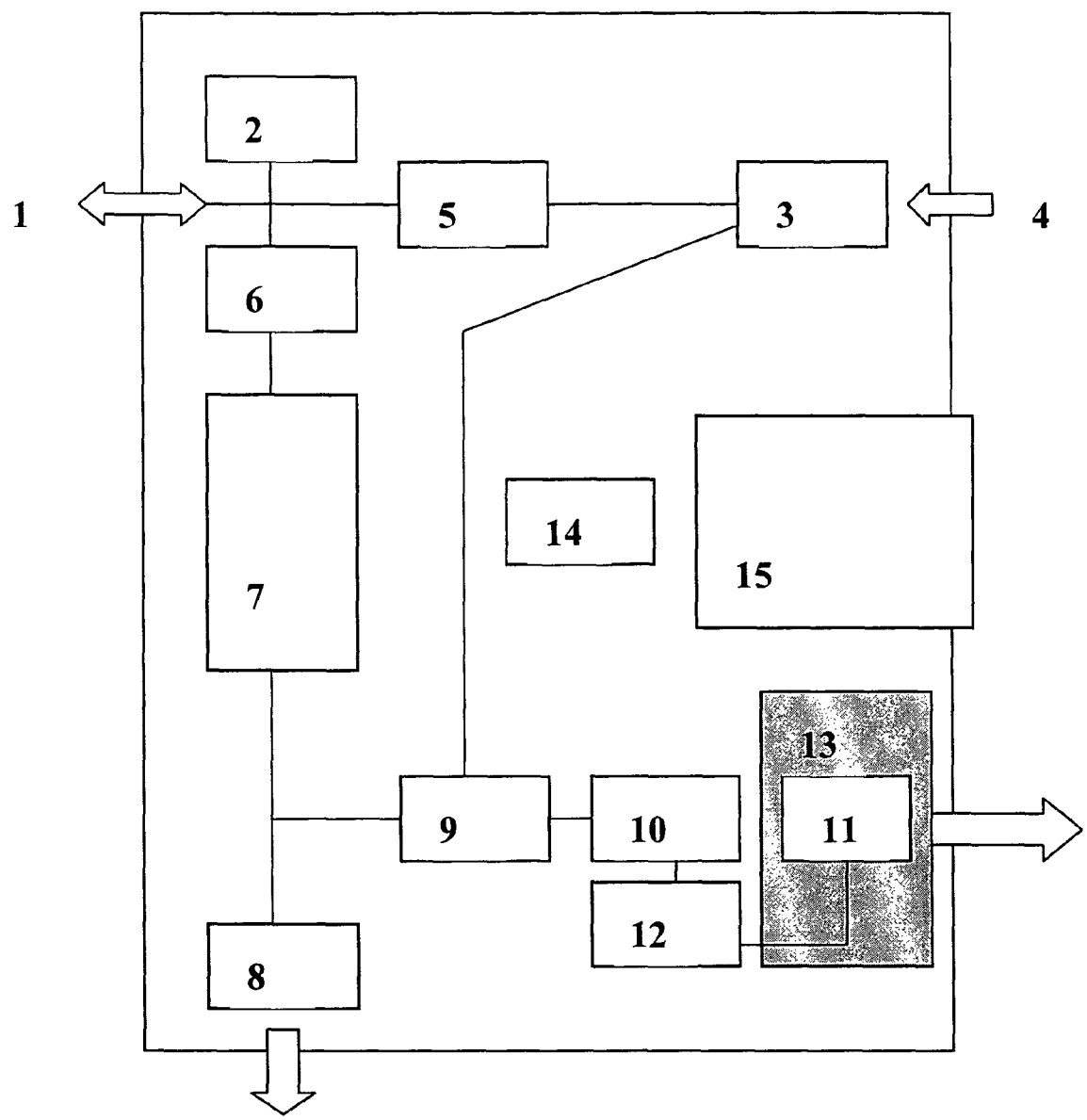

The present invention relates to the field of diagnostic gas analysis, and in particular to the determination of endogenous nitric oxide (NO) in exhaled breath of humans.

BACKGROUND OF THE INVENTION

The discovery of endogenous NO in exhaled air, and its use as a diagnostic marker of inflammation dates back to the early 1990 (See e.g. WO 93/05709; WO 95/02181). Today, the significance of endogenous NO is widely recognised, and since a few years back, a clinical analyser is available on the market (NIOX®, the first tailor-made NO analyser for routine clinical use with asthma patients, AEROCRINE AB, Solna, Sweden).

In the summer of 1997 the European Respiratory Journal published guidelines (ERS Task Force Report 10:1683-1693) for the standardisation of NO measurements in order to allow their rapid introduction into clinical practice. Also the American Thoracic Society (ATS) has published guidelines for clinical NO measurements (American Thoracic Society, Medical Section of the American Lung Association: Recommendations for standardized procedures for the online and offline measurement of exhaled lower respiratory nitric oxide and nasal nitric oxide in adults and children—1999, in *Am J Respir Crit Care Med,* 1999; 160:2104-2117). The NIOX® analyser for clinical use, and others mainly intended for research applications, are based on chemiluminescence determination of NO. While highly accurate and reliable, chemiluminescence determination of NO requires an advanced apparatus involving an ozone generator, a vacuum pump, means for dehumidification of the exhaled air, to mention only a few examples. Although the chemiluminescence analysers have developed significantly, they are still rather expensive and bulky.

PRIOR ART

WO 01/26547 discloses a handheld respiratory NO meter having a low resistance flow pathway throughout the device. Placed in this pathway is a NO concentration sensor generating electrical signals as a function of the instantaneous fraction of NO as the respiration gases pass through the flow pathway. The NO sensor is defined as a fluorescence based sensor having a response time preferably less than or equal to 200 ms, and most preferably less than or equal to 100 ms. Even faster response times are stated to be desirable.

While appealing as a concept, it appears to be practically very difficult if not impossible to achieve accurate and reliable NO determinations in the ppb range using a device according to WO 01/26547.

One objective of the present invention is to make available a portable, preferably handheld device, for diagnostic determinations of NO. Further aims include the goal to make the device easy to use, robust and reliable, while maintaining the high accuracy and sensitivity of the chemiluminescence analysers.

A further objective of the present invention is to make available an interface between the parameters dictated by physiological factors (e.g. exhalation flow rate, humidity, temperature etc), parameters dictated by standardized medical or diagnostic procedures (sample flow rate, duration etc), and sensor dependent parameters. Notably said physiological factors may vary between different individuals, depending on age, sex, bodyweight, and state of health. By the term sensor dependent parameters is hereby meant e.g. the temperature requirements of the sensor, the measurement time necessary for reliable measurements, high and low threshold values for humidity etc.

One particular objective of the present invention is to make available a device for diagnostic NO-measurements operating with an electrochemical sensor, which device is easily used in the clinics or at point-of-care, however without compromising the accuracy and reliability of the measurements.

Another objective is to make available a handheld and robust device, preferably also being a relatively low-cost device, again without compromising the accuracy and reliability of the measurements.

Further objectives, solved by the present invention, and advantages associated therewith will become evident from the following description and examples.

SUMMARY OF THE INVENTION

The objectives of the present invention are met by a device and method according to the attached claims. According to the invention, the device comprises at least one NO sensor, such as an electrochemical NO sensor, an inlet/outlet through which a patient inhales NO-free air through a scrubber, and exhales exhaled air at a predetermined flow rate and pressure, a buffer chamber for temporarily storing a portion of the exhaled air, and means for feeding said stored portion of the sample to said NO sensor during a period of time longer than the duration of the exhalation and/or at a flow rate much below the exhalation flow rate. The method includes at least the steps and operations corresponding to the above.

SHORT DESCRIPTION OF THE DRAWINGS

The invention will be described in closer detail in the following description, non-limiting examples, and claims, with reference to the attached drawings in which:

FIG. 1 shows schematically the components of a device according to the invention.

DESCRIPTION

The present inventors have surprisingly shown that an interface can be created between physiologically dictated parameters, as well as parameters dictated by standardized procedures, and the requirements of particular sensors.

This is illustrated by the device and method according to the present invention, where electrochemical sensor technology has been successfully applied in diagnostic measurements of NO.

It was however not possible to apply any NO sensor, such as an electrochemical sensor to NO measurements directly. At the present, electrochemical sensors have a considerably longer response time than other, hitherto used NO sensors, such as the commonly used chemiluminescence sensors. While a chemiluminescence sensor makes an instantaneous determination of the NO concentration in a gaseous sample, an electrochemical sensor requires longer time for establishing a stable signal. Further, electrochemical sensors suffer from high sensitivity to contaminants, sensitivity to variations in humidity, possible cross sensitivity to water or other compounds, low NO sensitivity, as well as a considerable temperature and flow dependence. If correctly calibrated, chemiluminescence sensors are also highly accurate, down to around ±1 ppb.

Consequently electrochemical sensors have hitherto not been used for diagnostic NO measurements, i.a. due to their long response time, and their relatively high detection levels (low sensitivity) and interference to other compounds.

As a result of the inventive efforts, it has surprisingly become possible to create a working interface between physiologically dictated parameters, as well as parameters dictated by standardized procedures, and the requirements of particular sensors. This made it possible to apply the electrochemical sensor technology to diagnostic NO measurements where a high reliability and accuracy in the lower ppb range (0 to 200 ppb, in particular in the range of 0 to about 50 ppb) is required, a novel device had to be developed.

In general terms, the device according to the invention has the following functionality and/or means for performing said functions (see also FIG. 1):

The device has a combined inlet/outlet 1, capable of engaging a disposable filter (not shown) through which the patient first inhales NO-free air via a built-in scrubber 3 removing NO from the ambient air, and then exhales, during which exhalation phase a sample is taken for NO-measurement and led to the sensor.

Preferably the inlet of the device is designed to tightly engage a disposable patient filter/mouthpiece filter. This filter may be a conventional filter, capable of ensuring viral/bacterial free air during normal inhalation, such as a 0.22µ filter. The filter is preferably a NIOX® PATIENT FILTER, marketed by Aerocrine AB, Solna, Sweden (Catalogue no. 02-1201).

The patient inhales clean, NO-free air through the mouthpiece/filter, and then exhales through the same filter, into the device. The filter thus fills two functions, as it both protects the patient and the device from particulate matter, viruses, bacterial, aerosols etc. The disposable filter has the added advantage of preventing spread of infections or patient-to-patient contagion.

In the vicinity of the inlet/outlet 1, a pressure sensor 2 is situated. The pressure sensor has the function of monitoring the breath, to ensure that the soft palate is closed during exhalation, to ensure that accurate exhalation pressure is maintained (the option of giving feed-back to the patient may be included) and to check that the inhalation of NO-free air is performed through the apparatus, i.e. through the NO-scrubber 3. The device also has an inlet 4 for ambient air, leading to said scrubber 3. The scrubber in turn is connected via a one-way valve 5 to the inlet/outlet 1, so that the patient can inhale NO-free air, but preventing exhaled air to pass said one-way valve.

The scrubber may be a conventional chemical NO scrubber, having an inlet and an outlet, and a main body filled with suitable filter media, e.g. a $KMnO_4$ based filter media, or a carbon based filter with suitable chemical additives. The construction of the filter, and arrangements for taking a zero sample is the subject of a co-pending patent application.

Further, in connection to the inlet/outlet 1 is a flow regulator 6, which has the function of controlling the exhalation flow with high accuracy to 20-800 ml/s, preferably 50 ml/s (±5 ml/s) when the user adapts to the feedback given by the device. Said flow regulator may be a passive flow restrictor, or an active regulator with means for measuring the flow and adjusting elements of said regulator, or by giving feed back to the patient, guiding the exhalation flow. According to one embodiment, the flow regulator automatically adjusts to the exhalation flow, limiting excess flow. According to another embodiment, the flow regulator is capable of adjusting to two or more pre-set levels of flow, during one exhalation, or during two or more subsequent exhalations.

The exhalation air is then led, through the flow regulator 6, to a buffer chamber 7, at the end of which a flush valve 8, and a three-way valve 9, are situated. During the initial phase of the exhalation, the flush valve 8 is open, and the three-way valve 9 closed, and the exhaled air is thus led to the ambient atmosphere. At a predetermined time, the flush valve 8 will close, and the three-way valve 9 open, so that the sample stored in the buffer chamber 7 will be led though the three-way valve 9, with the aid of a sample pump or fan 10, to the sensor 11.

The sensor may be any suitable NO sensor, e.g. a chemical, electrochemical, ultrasonic or other, preferably an electrochemical sensor.

According to a preferred embodiment of the invention, the sample pump 10 is a plunger pump. This type of pump has the advantages of being insensitive to variations in flow, and gives a low, even flow with high accuracy.

Before reaching the sensor, the sample is preferably led through means 12 for equalising the humidity of the sample to ambient conditions, and means 13 for equalising the temperature of the sample to the same stabilised temperature as that of the sensor, which, according to an embodiment, is controlled to a set temperature, different from the ambient temperature.

Preferably said means 13 acts to temperate both the sample and the sensor, e.g. by surrounding the sensor and by forming a large contact area for the gas flow. Alternatively, the temperature of the sample and/or that of the sensor is measured, and the results compensated for the temperature according to the specifications of the sensor.

The device further comprises means for controlling the functions of the above means, such as control electronics 14, which receive and analyse input e.g. from the sensors, and the user interface, and control the valves and the sample pump. The means 14 will also handle data acquisition, signal processing, data storage, communication with external units, and the user interface. External communication can be performed using one or several of the following options: a memory card or microprocessor card, an EEPROM card, in the following designated "smartcard", IR-communication, BLUETOOTH®, or other form of wireless communication, or via a conventional serial or parallel port.

The provision of a smartcard has among other advantages, the particular advantage that every patient is free to use any device according to the invention, and information relating to the patient will automatically be stored in the device, together with the measurement results. Simultaneously, information relating to the device and sensor will automatically be stored on the smartcard, together with the measurement results. This gives greatly added flexibility, without compromising the documentation requirements in diagnostic applications.

The device further comprises a user interface 15, one component of which has the form of a display, such as a liquid crystal display (LCD), preferably a touch screen, for displaying data to the user, and for receiving commands and settings from the user, e.g. for programming and/or parameter setting, functionality check or similar, performed by a qualified user, or by specifically designated service staff. Alternatively, these functions or part thereof may be performed through a conventional PC-interface, e.g. a conventional serial port (e.g. a USB port), or a parallel port.

The device preferably also comprises means for keeping track of current date and time, as well as means for setting the current date and time. There is preferably also an alarm function, which can be set for single or recurrent alarms, for example a specific time every day. It is possible to set the alarm time and recurrence, as well as to enable/disable the alarm. The alarm function has the advantage of improving patient compliancy with regard to monitoring their condition, and hopefully also with regard to the treatment of the same.

In summary, the input reaching the means 14 consist of signals from the pressure sensor, the NO sensor, the user interface, external communication interfaces, and the temperature control. The output leaving the means 14 consist of signals regulating the position of the flush valve, the three-way valve, the sample pump, the temperature control and the user interface.

In the device according to the invention, the sample of exhalation air is collected in accordance with the standardised exhalation manoeuvre (See ERS Guidelines 1997, ATS Guidelines 1999, supra) where after it is temporarily stored in a buffer chamber, which makes it possible to expose the sensor to a zero-sample or a patient sample at a steady flow, during a prolonged period of time, in order to obtain an accurate response from the sensor.

The device according to the invention includes a buffer chamber, and means for filling said buffer chamber during controlled exhalation, thus taking a sample of exhaled air for NO measurement. The volume of said buffer chamber is chosen so that it is sufficient to hold a sample, which then can be delivered to the sensor during a prolonged period of time, e.g. a volume of 150 ml. The means for filling said buffer chamber may include a valve or a set of valves. The means for filling said buffer chamber with a sample of exhaled air is preferably a valve allowing exhaled air to fill the buffer chamber during a pre-set duration of the exhalation.

The means for supplying the sample to the sensor preferably consist of a sample pump or fan.

Further, there are means for supplying NO-free air to the sensor, said means preferably consisting of a pump or fan, drawing air through a NO-scrubber. This pump or fan may be identical to that supplying the sample to the sensor, the source of gas (patient sample/zero sample) being controlled by one or several valves.

When the buffer chamber is filled with the desired sample, said means for delivering the sample to the sensor is/are activated. Such means include a sample pump or fan, supplying the sensor with a flow of about 0.5 to 15 ml/s, preferably from about 2 to about 10 ml/s during a predetermined time, longer than the exhalation time. This time is set in relation to the properties of the sensor, its sensitivity and configuration. The time can be chosen in an interval of about 15 to about 300 s, and preferably when the flow is about 2 ml/s, the time will be about 30 s or about 50 s, depending on the properties of the sensor.

The buffer chamber is a space for temporarily storing a portion of exhaled breath, in order to deliver it to the sensor at a flow and during a duration of time, adapted to the response time of said sensor. Preferably said buffer chamber is a space, which meets at least one of the following requirements:
  no significant diffusion of NO into the walls of the buffer chamber
  no significant diffusion of substances which interfere with the NO measurement
  turbulent flow
  no significant adhesion of NO to the inner walls According to one embodiment of the invention, said buffer chamber is formed as a long channel with small cross-section, e.g. a maze with a round, elliptic, square or rectangular cross section, e.g. moulded in a block of thermoplastic material.

According to another embodiment, said buffer chamber is formed as a length of tubing of a suitable, inert material, such as polyolefine tubing.

According to yet another embodiment, said buffer chamber is formed as a cylinder with a movable end wall or piston. By operating said end wall or piston longitudinally, sample is aspirated into and displaced out from the cylinder. This embodiment can be exemplified by a syringe where the volume of the syringe corresponds to the volume of the sample to be taken, and the rate at which the piston displaces the sample is equal to the rate at which the sample is to be fed to the sensor.

According to yet another embodiment, said buffer chamber is formed as a bellows of a suitable material. The sample is allowed to enter the bellows, either by the pressure exerted by the patient when exhaling into the device, or aided by mechanically expanding the bellows. The sample is then displaced by mechanically compressing the bellows.

According to another embodiment, the buffer chamber is adapted for sequential storage, i.e. the storage of many sequential samples. The channel preferably has a geometry which maximizes turbulence in order to minimize mixing due to laminar layers, e.g. a channel with varying cross-section or having deliberate disturbances to flow.

In the determination of nitric oxide concentration using an electrochemical sensor, both the temperature of the sensor and the gas flow are critical factors. The temperature of the sensor influences its sensitivity, and consequently fluctuating temperatures between separate measurements will result in poor repeatability and reduced precision and/or accuracy. Correspondingly, the temperature of the gas flow, as it meets the surface of the sensor, will influence the temperature of the sensor, with the above consequences.

In the device according to the present invention, and in the corresponding method, the temperature may be registered, and the results adjusted to the temperature using a correlation factor. Preferably, the temperature of both the gas and the sensor is accurately controlled by enclosing the sensor in means which both temperate the sensor and the sample gas before it reaches the sensor. The construction of such means is the subject of a co-pending patent application.

Electrochemical sensors are known to be sensitive to fluctuations in humidity. The device according to the invention preferably includes means for equalising the humidity of the sampled exhalation air, as well as the zero sample, with ambient humidity. Such means may consist of a length of NAFION® tube, through which the sample is led (NAFION® is a perfluorinated polymer membrane, the trademark being the property of E.I. du Pont de Nemours & Co, Delaware, USA). The advantage of this lies in that the patient sample and the zero sample will have the same humidity when reaching the sensor.

Electrochemical sensors unfortunately tend to have a limited life span, due to the electrolyte depletion.

According to the method and device of the present invention, the life span of the sensor is subject of a two-fold consideration. The device is equipped with means capable of establishing the production date and/or calibration date and/or expiration date of the sensor, e.g. by reading such information stored in association to the sensor, preventing use of the sensor according to pre-set criteria, e.g. when the expiration date is reached.

The device is further equipped with means for registering the number of measurements performed with a sensor, and preventing use of the sensor according to pre-set criteria, e.g. detection or determination of necessary sensor parameters.

The above means and associated functions have the advantage of making it possible to guarantee that each measurement is performed with a well functioning sensor.

The device according to the present invention has a novel, greatly simplified visual interface. The visual interface comprises a display, which indicates the state of the device (e.g. ON/START UP/READY/BUSY/OFF etc.) and guides the user through the inhalation and/or exhalation, and presents the result of the measurement. This display is preferably a conventional display, such as a liquid crystal display (LCD). Most preferably said display is a so called touch screen.

The above functions can be further supported by visual and audible signals, such as one or more blinking light/-s, user messages on a display, signals consisting of different symbols or colours, an audible signal which changes in tone or rhythm, all depending on the state of the device, or on the performance of the patient when inhaling and/or exhaling. For example, the device may display one symbol or colour when in START UP mode, and another symbol or colour when the START UP mode is completed, and the device is ready for measurements or enters READY mode. Likewise, the device may display one first symbol or colour, either blinking or steady, when the user inhales and/or exhales incorrectly, and then another second symbol or colour or other signal, clearly distinguishable from said first symbol, colour or signal when the inhalation and/or exhalation is performed according to pre-set requirements, ensuring good repeatability of the measurements. Parameters to be controlled and associated to visual and/or audible signals include the duration and pressure of the inhalation, and the exhalation, respectively.

The above means and associated functionalities make the device suitable for use by all patients, either alone or under the supervision of medical personnel, e.g. their treating physician or a nurse, for point-of-care use, as well as for home use by individual patients, monitoring their disease.

The device according to the present invention is preferably capable of communicating with its surroundings in many ways. With the patient, the device will communicate audibly and/or visually, indicating basic functions, state of readiness, proper use (inhalation, exhalation) and the result of the measurement. It is possible e.g. to send configuration data between an external software and a smartcard via the device.

Further, the device preferably includes an IR port for communication with a computer, e.g. for storing patient data in a database, for further analysis of the data or a separate IR printer for measurement report print-out. The IR port may also work to incorporate the device in a local network, enabling the use of local printers or in other ways to handle measurement results and patient information.

The device according to the invention preferably also includes a smartcard interface for entering and storing individual patient data. When using the device outside a clinical setting, each user would be given a personal smartcard. Preferably the smartcards would be pre-programmed to contain the settings relevant for different patient groups, e.g. male, female, child, or the settings relevant to patients of different race, age or bodyweight, in order to account for differences in dead space, or other physiologic differences.

The NO measurement results would then be recorded on the internal device memory and on the smartcard, together with information regarding the identity of the device and sensor used in the measurement, the date and time of the measurement, and optionally the ambient temperature and humidity. According to one embodiment, the smartcard would be designed to carry the patient history, and NO levels, optionally together with information regarding medication, doses, disease parameters, and subjective information, such the state of health, assessed by the patient or by the treating physician or nurse.

According to another embodiment, the smartcard is configured while inserted in the device but using external software.

The device is preferably also capable of communicating with external software, installed on an external computer, such as a PC. It is then possible e.g. to send measurements and other stored data from a smartcard (via the inventive device) to said external software.

According to one embodiment, it is also possible to send measurement data and other stored data from the internal memory of the device to external software.

Likewise, according to another embodiment, it is also possible to download software updates to the inventive device from external software.

It is preferably further possible to send service and support parameters, such as an error log from the inventive device to external software.

The device according to the present invention may further include an AC/DC converter, preferably an external converted feeding the device with DC. The device may further contain a rechargeable battery, a power unit supplying the required voltage to the components of the device. A battery for memory and sensor back-up is also included in the system.

The device according to the invention preferably comprises an internal memory, preferably with the possibility to store data from at least 2000 measurements. Alternatively, or in addition to the internal memory, the device will be capable of recording information on a removable data medium, such as a so called smartcard, a memory card, a microprocessor card, an EEPROM, a mini disc, diskette, or the like. The data to be recorded in the internal memory and/or on a smartcard or similar may comprise:
  patient ID
  date and time of measurement
  measured $FE_{NO}$
  sensor ID No.
  device ID No.
  disease and comfort parameter inputs in an advanced operating mode
  medication parameter inputs in an advanced operating mode Optionally, when measurement data memory is full, a warning is issued and, following confirmation of said warning, the oldest data may be overwritten with new data.

Preferably also an error list is provided either in the internal memory, or on the smartcard, or in duplicate on both of these, consisting of at least the following entries:
  error number
  timestamp According to a preferred embodiment, patient configuration is stored on the smartcard. The patient information may be general information, relating to different patient groups, such as male/female, child/adult/elderly, and further information, if diagnostically relevant. Preferably the smartcards are colour coded, each colour corresponding to one patient group. Preferably the smartcards are printed with a clearly visible number or code, so that individual cards can be distinguished. Preferably the smartcards have an area where the name of the patient can be printed or hand-written.

The patient information may also be individual information, relating to a specific patient. In both cases, the information may comprise:
  recommended max $FE_{NO}$ value
  recommended min $FE_{NO}$ value
  one of the available patient age group modes (via chosen smartcard)

The internal memory of the device according to the invention is preferably able to store both NO measurements and user input, including input e.g. by manufacturer and information for maintenance personnel. For example, the device is able to store errors to said internal memory.

The device is preferably also able to store configuration parameters to the internal memory, such as:
  production date
  calibration date
  sensor input calibration parameters The device is preferably also able to store settings and operating parameters to the internal memory, such as:
  top LED intensity
  volume
  contrast
  alarm time
  current time and date According to a preferred embodiment, the electrochemical NO sensor is integrated to a circuit comprising a memory, in the following called "sensor memory". This is preferably a memory circuit of EEPROM-type. Said sensor memory is capable of communicating and/or interacting with the internal memory and control circuits of the device.

In other words, it will be possible to read data from the sensor memory, such as:
  sensor calibration data
  expiration date
  sensor depletion control parameters
  sensor integrity data It is also possible to count down the remaining number of measurements on sensor at the rate at which measurements are performed.

According to a preferred embodiment, the inventive device will be capable of indicating when the expiration date of the sensor is approaching, or when the remaining number of measurements reaches a predetermined low value, and alerting the user. When the expiration date is reached, or when the number of measurements exhausted, the device will block further use of the sensor and alert the user.

According to the invention, the device keeps track of current time and date. It will also be possible to set current time and date, and current time and date is retained during backup battery operation.

There are numerous advantages related to the provision of a sensor memory. One is safety, as the expiration date will be automatically checked, and the use of the sensor automatically blocked when this date is passed. Another safety issue is the automatic control of the number of measurement, where the use of the sensor is automatically blocked when a maximum number of measurements is reached.

There may also be provided a feature for measuring ambient NO levels with the device. The ambient measurement process may consist of ambient stabilization, ambient measure, zero stabilization and zero measure phases in mentioned order. The process is similar to that of the diagnostic NO measurement, with the exception that the sample pump is used to extract the sample directly from the ambient air.

The result of the measurement is calculated with account to calibration constants in order to obtain the ppb value.

The device according to the invention preferably includes means and functions for temperature control. According to one embodiment, the means for temperature control consist of a Peltier element. The sensor temperature is kept at value set in internal configuration memory: If the measured temperature is outside the set conditions for use, the element will be off.

The temperature will be considered invalid if it has been outside the controlled temperature range for a preset period of time. If the temperature is invalid for a preset period of time, an error message is issued.

According to the invention, pressure is always measured relative ambient pressure. Ambient pressure is defined as the pressure when the user requests a measurement. During a pre-set duration of the inhalation, the pressure is required to be maintained below a value set in the internal configuration memory. During the exhalation phase, the pressure is further required to be maintained within max and min values set in the internal configuration memory. During the exhalation phase, a warning will be issued if the pressure is not within the range defined by high and low values set in the internal configuration memory. During the processing phase, after a preset transition time, the pressure is required to remain at ambient level.

According to one embodiment, the device includes a smartcard interface. The smartcard is inserted by the user when activating the device or before a measurement is performed, and is to remain inserted during the entire measurement process. If there is less than 10% free measurement storage capacity on said smartcard, the user will be notified before measurement.

The device and method according to the invention preferably also comprises a self-test function. If self-test fails an error message will be issued.

According to one embodiment, errors are always logged to database on main board memory. If a patient smartcard is inserted when an error occurs, the error will be logged to smartcard.

Importantly, the user will be notified when an error occurs.

The device and method according to the present invention offers many advantages. Numerous sources of error are avoided, or minimized.

For example, as the device registers the negative pressure when a patient inhales through the device, and thus through the NO scrubber supplying NO free air, the correct performance of the inhalation is controlled. The pressure check is further supplemented by feedback, guiding the patient to perform a correct inhalation and exhalation, or informing the patient when the inhalation and exhalation was correct, and when the breathing maneuver were insufficient.

The device and method further have built-in means and functions or operations, which constantly ensure that the electrochemical sensor functions properly.

One major advantage of the device and method according to the invention is the fact that it becomes possible to take a sample from a patient according to parameters dictated by the physiology of said patient, and according to parameters dictated by standardized procedures valid in medicine and diagnostics, while performing the analysis of the sample according to parameters optimal for the chosen sensor.

This is here illustrated by a device for the analysis of NO in exhaled breath using an electrochemical sensor, but the present invention is also applicable to the analysis of NO or other components, in samples other than exhaled air.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The invention claimed is:

1. A device for diagnostic NO measurements, the device comprising:
  a combined inlet and outlet configured to provide NO-scrubbed inhalation air to a patient and to accept an exhalation air at an exhalation flow rate;

a NO scrubber connected to the combined inlet and outlet along an inhalation flow path, the NO scrubber configured to provide NO-scrubbed air to the combined inlet and outlet;

a buffer chamber connected to the combined inlet and outlet along an exhalation flow path, the buffer chamber configured to temporarily hold a sample of the exhalation air for a period of time;

a flow regulator positioned between the combined inlet and outlet and the buffer chamber, the flow regulator configured to control the exhalation flow rate to 20-800 ml/s;

an electrochemical NO sensor connected to the buffer chamber, the electrochemical sensor configured to receive the sample of exhalation air temporarily held by the buffer chamber; and means for feeding the temporarily held sample of the exhalation air from the buffer chamber to the electrochemical NO sensor at a suitable flow rate for the electrochemical NO sensor, wherein the suitable flow rate for the electrochemical NO sensor is lower than the exhalation flow rate.

2. The device according to claim 1, wherein the suitable flow rate for the electrochemical NO sensor is about 0.5 to 15 ml/s.

3. The device according to claim 1, wherein the device comprises means for equalizing the humidity of the sample.

4. The device according to claim 3, wherein said means for equalizing the humidity of the sample comprises a length of tube, made from a catalytic membrane material.

5. The device according to claim 1, wherein the device further comprises control electronics for verifying the parameters of the inhalation and controlling the parameters of exhalation.

6. The device according to claim 5, wherein said control electronics comprise a pressure sensor and means for giving feedback to the patient.

7. The device according to claim 5, wherein said control electronics further comprise a flow sensor and means for controlling the flow and/or giving feedback to the patient.

8. The device according to claim 5, wherein said control electronics further comprise a pressure sensor capable of measuring absolute pressure in order to make it possible to compensate for varying partial pressure of NO depending on variations in ambient pressure.

9. The device according to claim 1, wherein the buffer chamber comprises a cylinder with a movable piston.

10. The device according to claim 1, wherein the buffer chamber comprises a length of tube.

11. A method for diagnostic NO measurements, the method comprising the steps of:

a patient inhales through an inhalation flow path of a device comprising a flow regulator, an electrochemical NO sensor, a NO scrubber, and a buffer chamber, said patient exhales air into an exhalation flow path of said device, wherein an exhalation flow rate and pressure is controlled to a preset value between 20-800 ml/s by the flow regulator, a sample of the exhaled air from said patient is temporarily held for a period of time in said buffer chamber, said sample is fed to said electrochemical NO sensor at a flow rate lower than the exhalation flow rate, and an NO concentration is determined in said sample.

12. A method according to claim 11, wherein the patient inhales NO-free air prior to exhaling into the device.

13. A method according to claim 11, wherein the patient inhales through the NO-scrubber integrated in said device, supplying NO-free air to the patient, prior to exhaling into the device.

14. A method according to claim 11, wherein the patient is given audible or visual feedback during the inhalation and exhalation steps, in order to support the correct performance of said steps.

15. A method according to claim 11, wherein the rate at which the sample is fed to the sensor is about 0.5 to 15 ml/s.

16. A method according to claim 11, wherein the device comprising an electrochemical NO sensor further comprises a user interface, wherein at least one of the following steps is included:

the patient enters information relating to his/her intake of a medicament into the user interface; and the patient subjectively assesses his/her state of health and enters corresponding information into the user interface.

17. A computer program comprising instructions for performing the method according to claim 11, wherein the instructions are stored in a computer-readable medium.

18. A method for diagnostic determination of NO in a gas sample, the method comprising the steps of:

introducing a sample at a first flow rate into the device of claim 1;

storing said sample in the buffer chamber temporarily;

feeding said sample to the electrochemical NO sensor at a second flow rate;

wherein the first flow rate is higher than the second flow rate.

19. The device according to claim 1, wherein the flow regulator is configured control the flow rate of the exhalation air to the buffer chamber at a rate of 45-55 ml/s.

20. The device of claim 1, further comprising an ambient air inlet connected to the NO scrubber, wherein the ambient air inlet and the combined inlet and outlet are separate structures.

* * * * *